(12) United States Patent
Agarie et al.

(10) Patent No.: US 8,101,824 B2
(45) Date of Patent: Jan. 24, 2012

(54) METHOD OF CONSTRUCTING TRANSGENIC ICE PLANT

(75) Inventors: Sakae Agarie, Saga (JP); Akihiro Nose, Saga (JP); Toyoaki Anai, Saga (JP); Haruki Sunagawa, Saga (JP); Makiko Umemoto, Saga (JP)

(73) Assignee: Saga University, Saga (JP)

( * ) Notice: Subject to any disclaimer, the term of this patent is extended or adjusted under 35 U.S.C. 154(b) by 696 days.

(21) Appl. No.: 11/918,224

(22) PCT Filed: Apr. 15, 2005

(86) PCT No.: PCT/JP2005/007670
§ 371 (c)(1),
(2), (4) Date: Jan. 9, 2008

(87) PCT Pub. No.: WO2006/112034
PCT Pub. Date: Oct. 26, 2006

(65) Prior Publication Data
US 2009/0217410 A1   Aug. 27, 2009

(51) Int. Cl.
*C12N 15/84* (2006.01)
*A01H 4/00* (2006.01)
*A01H 5/00* (2006.01)

(52) U.S. Cl. ......... 800/294; 435/430; 435/431; 435/469

(58) Field of Classification Search ..................... None
See application file for complete search history.

(56) References Cited

FOREIGN PATENT DOCUMENTS

| | | |
|---|---|---|
| EP | 1050209 A2 | 11/2000 |
| EP | 1264886 A1 | 12/2002 |
| JP | 10-501139 A | 2/1998 |
| JP | 2000-316403 A | 11/2000 |
| JP | 2002-291360 A | 10/2002 |
| JP | 2003-274954 A | 9/2003 |
| JP | 2004-357574 A | 12/2004 |
| WO | WO 95/34667 A2 | 12/1995 |
| WO | WO 01/64865 A1 | 9/2001 |

OTHER PUBLICATIONS

Meiners et al. Plant Cell Reports 9(10): 563-566 (Feb. 1991).*
Schaeffer et al. Plant Molecular Biology 28: 205-218 (1995).*
Higashie et al., "Ice Plant (Mesembryanthemum crystallinum L.) Keishitsu Tenkantai Sakushutsuho no Kakuritsu," Crop Science Society of Japan Koenkai Yoshi • Shiryoshu (2004), vol. 218, pp. 352-353.
Sunagawa et al., "Tagatai Keisei ni yoru Ice Plant (Mesembryanthemum crystallinum L.) no Saibunka," Crop Science Society of Japan Koenkai Yoshi • Shiryoshu (2004), vol. 218, pp. 250-251.
Andolfatto, Peter et al. "Transformed hair roots of *Mesembryanthemum crystallinum*: gene expression patterns upon salt stress" Phisysiologia Plantarum vol. 90: p. 708-714, 1994.
Ishamaru, Ken et al. "Transformation of a CAM plant, the facultative halophyte Mesembryanthemum crystallinum by Agrobacterium tumefaciens" Plant Cell, Tissue and Organ Culture vol. 57, pp. 61-63, 1999.
Cushman, J.C. et al. "Efficient plant regeneration of Mesembryanthemum crystallinum via somatic embrogenesis" Plant Cell Reports vol. 19 pp. 459-463, 2000.

* cited by examiner

*Primary Examiner* — David T Fox
(74) *Attorney, Agent, or Firm* — Birch, Stewart, Kolasch & Birch, LLP

(57) ABSTRACT

The present invention provides a method of transforming common ice plant by gene transfer using a microorganism belonging to the genus *Agrobacterium* and a method of producing a transformed common ice plant. The present invention also provides a stable transformed common ice plant.

8 Claims, 3 Drawing Sheets

SEQUENCE LISTING

```
<160> NUMBER OF SEQ ID NOS: 2

<210> SEQ ID NO 1
<211> LENGTH: 30
<212> TYPE: DNA
<213> ORGANISM: Artificial Sequence
<220> FEATURE:
<223> OTHER INFORMATION: Synthetic primer

<400> SEQUENCE: 1
gtggagaggc tattcggcta tgactgggca                                      30
```

```
<210> SEQ ID NO 2
<211> LENGTH: 30
<212> TYPE: DNA
<213> ORGANISM: Artificial Sequence
<220> FEATURE:
<223> OTHER INFORMATION: Synthetic primer

<400> SEQUENCE: 2
tcatagaagg cggcggtgga atcgaaatct                                    30
```

METHOD OF CONSTRUCTING TRANSGENIC ICE PLANT

This application is the national stage of PCT/JP2005/007670 filed on Apr. 15, 2005.

TECHNICAL FIELD

The present invention relates to a method of transforming common ice plant; a method of producing a transformed common ice plant; and a transformed common ice plant.

BACKGROUND ART

Common ice plant (*Mesembryanthemum crystallinum* L.) is an annual plant belonging to the genus *Mesembryanthemum* in the family Aizoaceae and a halophyte capable of growing in seawater-containing soil. Generally, a halophyte refers to a special plant with high salt tolerance which is capable of growing in the soil containing 100 mM NaCl where ordinary plants (glycophyte) can not grow. Common ice plant has a high capacity of absorbing metals such as Cd and Cu, and inorganic salts such as NaCl. For example, it is said that common ice plant is capable of absorbing about 15 g of NaCl per plant. This corresponds to 200 g/m$^2$ or 2 t/ha.

At present, about 10% of the total agricultural area in the world suffers from salt accumulation which makes agriculture difficult. In Japan, there is the same problem. In particular, in Saga Prefecture the problem is more serious because as large as about 65% of its agricultural area is originally reclaimed land.

Common ice plant switches its mode of photosynthesis from C3 (which is seen in soybean, rice, etc.) to CAM (which is seen in orchid and cactus, etc.) under unfavorable environments such as salts, high light and drought. The common ice plant has become a target of various studies as a model plant for elucidating the mechanisms of changes in photosynthesis and the abiotic stress tolerance. Recently, as performed in well-known model plants such as rice and *Arabidopsis thaliana*, analysis of the whole nucleotide sequence of the genomic DNA is going to be performed in the common ice plant. Therefore, in the near future when functional analysis of various genes or creation of transgenic ice plants will be performed based on the determined nucleotide sequence, transformation of common ice plant will be essential as in the cases of other model plants. Further, for such purposes, an efficient transformation protocol of the common ice plant will be extremely important.

As methods for transforming plants, generally, direct methods such as particle bombardment, electroporation and the polyethylene glycol (PEG) method, and indirect methods such as a gene transfer using a microorganism belonging to the genus *Agrobacterium* (hereinafter, sometimes simply referred to as "an *Agrobacterium*") are known. However, particle bombardment has the following problems: (i) gene transfer is limited to surface cells; (ii) recombination and deletion are apt. to occur in the final transferred fragments; (iii) transformed plants often turn out chimeric; (v) expensive instruments are necessary; (v) since fine metal particles are scattered, human body may be endangered. Electroporation has the following problems: (i) since DNA transfer through cell walls is not easy as in bacteria, decrease in transfer efficiency and cell damage are unavoidable; (ii) since protoplast is the target for gene transfer, electroporation is inapplicable to those plant species in which a protoplast-to-plantlet regeneration system has not been established; thus, application frequency is extremely low; (iii) since a long culture period is required, mutation ratio increases and the probability to obtain normal transformants of interest decreases. The PEG method has similar problems to those seen in electroporation (e.g., decrease in transfer efficiency (actually, the efficiency further decreases) and cell damage are unavoidable). Therefore, at present, it is believed that gene transfer using an *Agrobacterium* is most secure and useful. In this method, it is possible to integrate a DNA of interest (recombinant gene, etc.) into the plant genome by using the *Agrobacterium* itself as a biological vector and utilizing the recombinant sequence (T-DNA region) and recombinant enzymes possessed by this bacterium.

Gene transfer using an *Agrobacterium* has been established to date in various plant species, and a large number of stable transformants have been produced.

With respect to the common ice plant, however, gene transfer into root apex cells and cultured cells (Andolfatto et al., Physiol. Plant., vol. 90, pp. 708-714 (1994); Ishimaru, Plant Cell Tissue Organ Culture, vol. 57, pp. 61-63 (1999)) suggest that *Agrobacterium* is able to infect the common ice plant cells (i.e., transfer of a foreign gene is possible), subsequent regeneration ratios were extremely low (Cushman et al., Plant Cell Rep., vol. 19, pp. 459-463 (2000)) and stable transformants have not yet been achieved.

DISCLOSURE OF THE INVENTION

An object of the present invention is to provide a method of transforming common ice plant by gene transfer using a microorganism belonging to the genus *Agrobacterium*; a method of producing a transgenic common ice plant; and a stable transformation of the common ice plant.

As a result of intensive and extensive researches toward the solution of the above problem, the present inventors have found that the regeneration activity of a specific tissue in the common ice plant is extremely high compared to other tissues or callus and that, by using this specific tissue as a target of infection by a microorganism belonging to the genus *Agrobacterium*, common ice plant can be transformed and the transformants of the common ice plant can be produced easily. Thus, the present invention has been achieved.

Briefly, the present invention is as described below.
(1) A method of transforming common ice plant, comprising a step of transforming a cotyledonary node of common ice plant with a microorganism belonging to the genus *Agrobacterium* containing a desired gene.

In the above-described transformation method, the cotyledonary node may be, for example, a cotyledonary node of a plantlet (seeding). The plantlet may be, for example, a plantlet 4 to 10 days after seeding.
(2) A method of producing a transformed common ice plant, comprising growing the resultant cotyledonary node obtained by the transformation method of (1) described above in the presence of a plant hormone(s).

In the above-described production method, the plant hormone may be at least one selected from the group consisting of thidiazuron (TDZ), forchlorfenuron (CPPU), benzyladenine (BA) and naphthalene-1-acetic acid (NAA). The concentration (total concentration) of the plant hormone may be, for example, 0.1-10 mg/L. Especially, the concentration of thidiazuron may be, for example, 0.1-5 mg/L.
(3) A transformed common ice plant obtained by the production method of (2) described above.

BEST MODES FOR CARRYING OUT THE INVENTION

Figure 1:
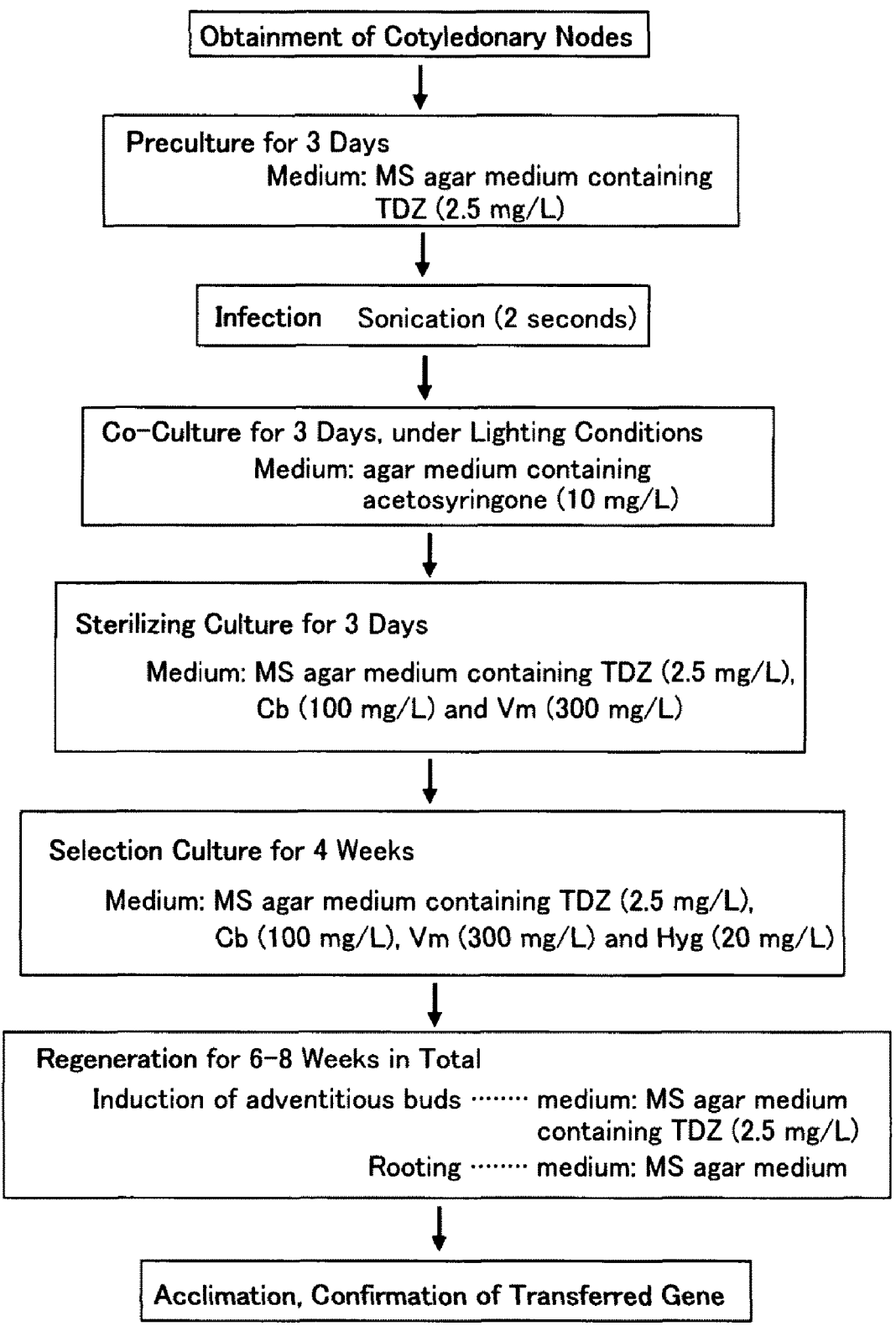
FIG. 1 is an outline diagram of the procedures for producing a transformed common ice plant using an *Agrobacterium* performed in Example 1.

Hereinbelow, the present invention will be described in detail. However, the scope of the present invention is not bound by these descriptions, and the present invention is not limited to the working Examples provided later and may be practiced with appropriate modifications without departure from the spirit of the present invention. All documents cited herein for explaining the present invention are incorporated herein by reference in their entirety.

1. Outline

The present invention relates to a method of transforming common ice plant and a method of producing common ice plant transformants. These methods of the present invention for the first time made it possible to produce a stable, transformed common ice plant, and thus they have extremely high utility value. The reason why common ice plant transformants could not be obtained is because regeneration from *Agrobacterium*-infected tissues to plantlets was not performed efficiently and surely.

Usually, a plant material (a tissue or the like which is to be infected) used in *Agrobacterium*-mediated transformation varies depending on the type of the plant. In a special case as seen in the model plant *Arabidopsis thaliana*, flower organs or wounded growing points are infected with an *Agrobacterium*. However, generally, a cultured tissue in the process of dedifferentiation or after dedifferentiation (the so-called callus) is used in many cases as a material for the above purpose. When such a cultured tissue is used, usually, 3 to 4 weeks of dedifferentiation induction period is required in order to prepare the tissue before infection. After infection, several weeks are required further in order to regeneration of the tissue to a whole plant. Thus, this method lacks rapidity. Besides, somatic cell mutations may occur in the dedifferentiation process and the process of inducing redifferentiated plantlets from callus.

To date, attempts to redifferentiate various tissues or organs such as the hypocotyl (stem part of plantlets) or root into plantlets have been made in common ice plant. However, in any of these attempts, the regeneration efficiency was very low and it was extremely difficult to obtain a transformant.

Under circumstances, the present inventors repeated experiments and examinations to find suitable explants obtained from various tissues and organs (root, stem, leaf, etc.) of common ice plant having high regeneration capacity. As a result, the present inventors have found that the regeneration activity of a specific tissue (e.g., cotyledonary nodes, preferably cotyledonary nodes of young seedlings (plantlets)) is extremely high and that by transforming common ice plant using this specific tissue as a target of infection, common ice plant transformants can be obtained easily. The present invention has been achieved based on these findings.

The present inventors have also found that, when the above-mentioned specific tissue is cultured (at least after infection) in the presence of specific plant hormones (such as thidiazuron), the regeneration activity of the tissue is further improved and common ice plant transformants can be obtained more efficiently 2. Method of Transforming Common Ice Plant The method of transforming common ice plant of the present invention is, as described above, characterized by comprising a step of transforming cotyledonary nodes of common ice plant with a microorganism belonging to the genus *Agrobacterium* (an *Agrobacterium*) containing a desired gene. Specifically, the method of the present invention is characterized by infecting cotyledonary nodes obtained from common ice plant with an *Agrobacterium* containing a desired gene and then culturing the cotyledonary nodes in the presence of the bacterium (microorganism).

Hereinbelow, one embodiment of the transformation method of the present invention will be described following individual steps. However, the method of the present invention is not limited to a method consisting of these steps alone. The method of the present invention may further include other steps within the scope of technical commonsense and creative ability of those skilled in the art.

(1) Obtainment of Cotyledonary Nodes

In the transformation method of the present invention, it is important to use the cotyledonary node of common ice plant as a target tissue to be infected with an *Agrobacterium*. The "cotyledonary node" refers to the part at which the two cotyledons of dicotyledonous plants (including common ice plant) are joined together. This part contains the growing point for new leaves.

For obtaining cotyledonary nodes, first, common ice plant seeds must be seeded and germinated. As a medium for germination, a known medium may be used without particular limitation. For example, MS agar medium may be enumerated. Optionally, a filter paper wetted with water may be used preferably.

As a culture vessel, a known vessel may be used without particular limitation. For example, a glass or plastic dish may be used in any of the culture steps of the method of the present invention.

The cotyledonary node used in the transformation method of the present invention is not particularly limited. Preferably, cotyledonary nodes from seedlings of common ice plant are used. Specifically, seedlings at 4 to 10 days after germination are preferable, and seedlings of 5 to 7 days after germination seeding are more preferably. Seedlings satisfying the above range are desirable because cotyledonary nodes with still higher redifferentiation activity can be obtained therefrom.

The method for obtaining cotyledonary nodes is not particularly limited. Preferably, a method may be used in which the region of cotyledonary node (preferably, one of the cotyledons as a whole with the cotyledonary node) is removed with tweezers and a knife in a glass dish or the like under microscopic observation at the cotyledon leafing stage of common ice plant shoots.

The number of cotyledonary nodes to be obtained (i.e., the number of cotyledonary nodes to be used in the subsequent preculture step) is not particularly limited. Preferably 20-100, more preferably 40-50 cotyledonary nodes may be used. When the number satisfies the above range, it is preferable because cotyledonary nodes may be cultured in the subsequent step in a dish with appropriate space between them.

(2) Preculture of Cotyledonary Nodes

Preculture step aims at culturing the thus obtained cotyledonary nodes (more specifically, cotyledons including cotyledonary nodes) so that they grow to an appropriate cultured tissue that may be used in the subsequent infection step. In this step, generally, it is preferable to culture the obtained cotyledonary nodes until they form small shoots.

As a medium for preculture, a known medium may be used without particular limitation. For example, a medium used for germination (e.g., MS agar medium) may be used preferably.

The above medium preferably contains plant hormones. Specifically, the medium contains at least one selected from the group consisting of thidiazuron (TDZ), forchlorfenuron (CPPU), benzyladenine (BA), and naphthalene-1-acetic acid (NAA) are preferably used. More preferably, the medium contains thidiazuron. Still more preferably, the medium contains thidiazuron and naphthalene-1-acetic acid. By containing these plant hormones, in particular thidiazuron, the number of shoot differentiation increases; the healthiness of shoots is retained; and eventually, regeneration is promoted.

The concentration of the above plant hormones (total concentration) is preferably 0.1-10 mg/L, more preferably 0.5-10 mg/L, still more preferably 1-10 mg/L and especially preferably 1-6 mg/L, relative to the total medium. With respect to TDZ, the concentration is preferably 0.1-5 mg/L, more preferably 0.5-5 mg/L, still more preferably 1-5 mg/L and especially preferably 2.5-5 mg/L, relative to the total medium. With respect to CPPU, the concentration is preferably 0.1-5.0 mg/L, more preferably 1.0-5.0 mg/L and still more preferably 2.5-5 mg/L, relative to the total medium. With respect to BA, the concentration is preferably 0.1-20 mg/L, more preferably 1.0-10 mg/L and still more preferably 1.0-5 mg/L, relative to the total medium. With respect to NAA, the concentration is preferably 0.1-10 mg/L, more preferably 0.1-5 mg/L and still more preferably 0.1-1 mg/L, relative to the total medium.

Preculture is preferably performed under lighting. The light intensity is not particularly limited. Any intensity may be used as long as plants are capable of growing healthily at that intensity. For example, 50-100 $\mu mol \cdot m^{-2} \cdot s^{-1}$ may be preferable.

The culture temperature in preculture is preferably 20-33° C., more preferably 25-30° C., for example.

The period for preculture is preferably 1-10 days, more preferably 3-5 days, for example. Preculture may be terminated appropriately at a stage when a cultured tissue that may be used in the subsequent infection step has been obtained or may be terminated at any stage thereafter (usually, 3 days after the start of preculture).

(3) Infection in Cotyledonary Nodes with an *Agrobacterium*

Infection step aims at infecting the cultured tissue (more specifically, cells of the cultured tissue), which is obtained in the preculture step with a microorganism belonging to the genus *Agrobacterium* (an *Agrobacterium*) containing a desired gene.

As the *Agrobacterium* used in this infection step, those bacteria harboring Ti plasmid or Ri plasmid that have been conventionally used in transformation of dicotyledonous plants may be given. Among all, *Agrobacterium tumefaciens* is preferable. A great number of these Agrobacteria carry a plasmid vector comprising the vir region (or a DNA derived therefrom) of Ti plasmid derived from *Agrobacterium tumefaciens*. A desired gene carrying the character to be conferred to a target plant may be inserted into this vector. Alternatively, a desired gene may be present in another vector (such as pBR322) and inserted into Ti plasmid in vivo by homologous recombination or the like. Therefore, in the present invention, a desired gene to be transferred into the genome of cultured tissue cells is inserted (located) between the border sequences of T region in the same manner as in conventional methods. In this case, the desired gene may be inserted into Ti plasmid in the *Agrobacterium* or into other plasmid. Insertion of a desired gene into various plasmids may be preformed based on information such as GenBank accession numbers and appropriately using genetic recombination technology well known to those skilled in the art (for example, see "Molecular Cloning" 2nd ed., Sambrook, J., et al., Cold Spring Harbor Laboratory Press U.S.A., 1989).

The "desired gene" in the present invention is preferably, but is not limited to, a DNA comprising a DNA encoding a desired protein which is to be expressed in common ice plant cells, and DNAs necessary for transcription and translation of the above DNA. The desired gene may consist of the DNA encoding the desired protein alone, or may be any oligonucleotide or polynucleotide. Generally, it is preferable to allow the "desired gene" to contain a selectable marker (such as $Hyg^r$ and $Km^r$) that shows resistance to a specific antibiotic, in order to facilitate the selection of transformants from non-transformants in the selection culture step of the production method of the present invention described later.

Plasmid transfer into an *Agrobacterium* may be performed a known method using genetic recombination technology. For example, the triple cross technique for bacteria (Ditta, G et al., Proc. Natl. Acad. Sci. USA, vol. 77, pp. 7347-7351 (1980)) may be preferably used.

Culture of the *Agrobacterium* to be used in infection step may be performed by a conventional culture method. Non-limitative example of preferable culture method includes a method in which cells of the *Agrobacterium* are taken from a bacterial stock (e.g., glycerol stock (−80° C.)) with a sterilized platinum loop or the like, coated on an appropriate medium (such as AB medium) and cultured in dark (e.g., for 3 days at 28° C.).

The method of infecting cotyledonary nodes with the *Agrobacterium* is not particularly limited. For example, the following methods are preferable. (i) A method in which cultured *Agrobacterium* cells are suspended in a liquid medium for infection treatment containing TDZ, acetosyringone, and inorganic salts for MS medium; then, precultured cotyledonary nodes are soaked in this suspension and sonicated. (ii) In method (i) described above, vacuum infiltration treatment is carried out instead of sonication. (iii) In method (i) or (ii) described above, sonication or vacuum infiltration treatment is not carried out; a surfactant is added to the liquid medium for infection treatment and cells are soaked in this medium for a specific period of time. (iv) In method (i) or (ii) described above, sonication or vacuum infiltration treatment is not carried out; cells are soaked in the liquid medium for infection treatment (without addition of a surfactant). In the present invention, method (i) described above is more preferable.

In method (i) described above, sonication time is not particularly limited, but preferably 0.2-60 seconds, more preferably 2 seconds. When the irradiation time is within the above range, it is preferable because explant tissue is not destroyed. The soaking time (including sonication time) is not particularly limited, but preferably 5-20 minutes, more preferably 5-6 minutes. When the soaking time is within the above range, it is preferable because the amount of adhesion of *Agrobacterium* will be an appropriate amount.

(4) Co-Culture after Infection

Co-culture step aims at culturing the infected cotyledonary nodes in the presence of the *Agrobacterium*. Through the above-described infection step and this co-culture step, it is possible to integrate a desired gene (foreign gene) into the genome of cells of cotyledonary nodes as a cultured tissue (i.e., to transform common ice plant).

In this co-culture step, prior to the start of co-culture, it is preferable to remove excessive bacterial cells and moisture by, for example, pouring the suspension after the infection step onto a dry sterilized filter paper together with the cotyledonary nodes and then transferring the cotyledonary nodes alone onto a fresh sterilized filter paper.

As a medium for co-culture, a known medium may be used. Preferable examples include, but are not limited to, a medium used in the preculture step (e.g., MS agar medium) supplemented with acetosyringone, a medium used in the preculture step supplemented with appropriate concentrations of plant hormones and acetosyringone, and an agar medium containing acetosyringone and water alone.

Co-culture may be performed either under lighting conditions or under darkness. Co-culture under lighting conditions is preferable because the healthiness of cotyledonary nodes is maintained due to photosynthesis and thus the damage caused by *Agrobacterium* infection can be suppressed. Lighting conditions at the time of co-culture are not particularly limited. In order to obtain the above-mentioned effects more efficiently, the lighting conditions are preferably 50-200 μmol·m$^{-2}$·s$^{-1}$, more preferably 50-70 μmol·m$^{-2}$·s$^{-1}$.

The culture temperature in the co-culture is preferably 18-33° C., more preferably 25-30° C., for example.

The period for co-culture is preferably 3-10 days, more preferably 3-5 days, but is not particularly limited. Co-culture may be appropriately terminated, for example, at the stage when enlargement of the cotyledonary node tissue is recognized slightly or at any stage thereafter (usually, 3 to 7 days after the start of co-culture).

In the above-described transformation method of the present invention, a particularly preferred embodiment may be given as follows: preculturing a tissue (cotyledonary nodes) for 3 days, sonicating the cultured tissue to thereby infect with an *Agrobacterium*, and then co-culturing the tissue and the *Agrobacterium* in a medium containing acetosyringone and water alone for 3 days under lighting conditions. In this embodiment, it is possible to obtain transformants.

3. Method of Producing Transformed Common Ice Plant

The method of producing a transformed common ice plant of the present invention is, as described earlier, a method characterized by growing the cotyledonary nodes obtained by the transformation method of the invention in the presence of a plant hormone(s). That is, the method of the present invention can be said a method of preparing a transformed common ice plant. Hereinbelow, one embodiment of the production method of the present invention will be described following individual steps. However, the production method of the present invention is not limited to a method consisting of these steps alone. The method of the present invention may further include other steps within the scope of technical commonsense and creative ability of those skilled in the art.

(1) Sterilizing Culture

Sterilizing culture step aims at culturing the cotyledonary nodes obtained by the above-described transformation method of the present invention in a medium containing appropriate antibiotics to thereby sterilize the co-existing *Agrobacterium* and obtaining the transformed cotyledonary nodes selectively.

As a medium for sterilizing culture, a known medium may be used without particular limitation. For example, a medium used in preculture step (e.g., MS agar medium) may be used preferably.

The antibiotics to be contained in the medium are preferably those antibiotics which inhibit the proliferation and/or growth of the *Agrobacterium* used in the transformation but do not substantially give adverse effect on the growth of cotyledonary nodes of common ice plant. Preferable examples include carbenicillin, vancomycin, claforan and augpenin. Among them, carbenicillin and vancomycin are more preferable. The concentrations of various antibiotics are not particularly limited and may be selected appropriately within the known range of effective concentration.

The medium preferably contains at least one plant hormone selected from the group consisting of thidiazuron (TDZ), forchlorfenuron (CPPU), benzyladenine (BA) and naphthalene-1-acetic acid (NAA). Among all, thidiazuron is more preferable.

The concentration of the above plant hormones (total concentration) is, for example, preferably 0.1-10 mg/L, more preferably 0.5-10 mg/L, still more preferably 1-10 mg/L and especially preferably 1-6 mg/L, relative to the total medium. With respect to TDZ, the concentration is preferably 0.1-5 mg/L, more preferably 0.5-5 mg/L, still more preferably 1-5 mg/L and especially preferably 2.5-5 mg/L, relative to the total medium. With respect to CPPU, the concentration is preferably 0.1-5.0 mg/L, more preferably 1.0-5.0 mg/L and still more preferably 2.5-5 mg/L, relative to the total medium. With respect to BA, the concentration is preferably 0.1-20 mg/L, more preferably 1.0-10 mg/L and still more preferably 1.0-5 mg/L, relative to the total medium. With respect to NAA, the concentration is preferably 0.1-10 mg/L, more preferably 0.1-5 mg/L and still more preferably 0.1-1 mg/L, relative to the total medium.

By selecting the concentration of plant hormones (in particular, thidiazuron) used in sterilizing culture step within the above range, it is possible to inhibit the development of tissues with distorted morphology. Thus, the growth of plant bodies is maintained well and, eventually, sterilization can be performed efficiently.

The culture temperature in sterilization culture is preferably 20-33° C., more preferably 20-25° C., for example.

The period for sterilizing culture is preferably 2-7 days, more preferably 3-5 days, but is not particularly limited. Sterilizing culture may be terminated, for example, at a stage when no growth of the *Agrobacterium* is observed on the medium with which cotyledonary nodes are contacting or on plant bodies, or at any stage thereafter (usually 3 to 5 days after the start of sterilizing culture).

(2) Selection Culture

Selection culture step aims at culturing the cotyledonary nodes obtained in the sterilizing culture step in a medium containing appropriate antibiotics and selectively obtaining those which are transformed by transfer of a desired gene (including a specific antibiotic resistance gene as a selectable marker) (i.e., transformants).

As a medium for selection culture, a known medium may be used without particular limitation. For example, a medium used in preculture step (e.g., MS agar medium) may be used preferably.

Among antibiotics to be contained in the medium, examples of antibiotics corresponding to the above selectable marker include, but are not limited to, hygromycin and kanamycin. Hygromycin is more preferable. Other antibiotics which may be used jointly in this step include the antibiotics used in the sterilizing culture. The concentration of various antibiotics is not particularly limited and may be appropriately selected within the known range of effective concentration.

The medium preferably contains at least one plant hormone selected from the group consisting of thidiazuron (TDZ), forchlorfenuron (CPPU), benzyladenine (BA) and naphthalene-1-acetic acid (NAA). Among all, thidiazuron is more preferable.

The concentration of the above plant hormones (total concentration) is, for example, preferably 0.1-10 mg/L, more preferably 0.5-10 mg/L, still more preferably 1-10 mg/L and especially preferably 1-6 mg/L, relative to the total medium. With respect to TDZ, the concentration is preferably 0.1-5 mg/L, more preferably 0.5-5 mg/L, still more preferably 1-5 mg/L and especially preferably 2.5-5 mg/L, relative to the total medium. With respect to CPPU, the concentration is preferably 0.1-5.0 mg/L, more preferably 1.0-5.0 mg/L and still more preferably 2.5-5 mg/L, relative to the total medium. With respect to BA, the concentration is preferably 0.1-20 mg/L, more preferably 1.0-10 mg/L and still more preferably 1.0-5 mg/L, relative to the total medium. With respect to NAA, the concentration is preferably 0.1-10 mg/L, more preferably 0.1-5 mg/L and still more preferably 0.1-1 mg/L, relative to the total medium.

By selecting the concentration of plant hormones (in particular, thidiazuron) used in selection culture step within the above range, the number of shoot differentiation increases and the healthiness of shoots is retained. As a result, effects such as promotion of redifferentiation are obtained.

Selection culture may be performed either under lighting conditions or under darkness. Culture under lighting conditions is preferable because healthy plant bodies highly resistant to antibiotics and Agrobacteria can be obtained by promotion of photosynthesis by light. Lighting conditions at the time of selection culture are not particularly limited. From the viewpoint of the above effect, the lighting conditions are preferably 50-200 µmol·m$^{-2}$·s$^{-1}$, more preferably 50-70 µmol·m$^{-2}$·s$^{-1}$.

The culture temperature in selection culture is preferably 20-33° C., more preferably 20-25° C., for example.

The period for selection culture is preferably 3-6 weeks, more preferably 4-5 weeks, but is not particularly limited. Selection culture may be terminated appropriately, for example, at a stage when living plants and dead plants become discriminated definitely or at any stage thereafter (usually, 3 to 4 weeks after the start of selection culture).

(3) Regeneration

Regeneration step aims at culturing the cotyledonary node obtained in the selection culture step further, allowing to promote various organ formation or tissue formation (such as adventitious bud induction and rooting) utilizing the high regeneration activity of cotyledonary node, and obtaining transformants of common ice plant as a stable intact plant (plantlet or adult plant).

As a culture medium for regeneration, a known medium may be used for either adventitious bud formation or rooting. For example, a medium used in the preculture step (e.g., MS agar medium) may be used preferably.

Generally, culture for regeneration is preferably performed aseptically without using antibiotics. However, various antibiotics such as hygromycin and kanamycin may be used appropriately at known effective concentrations.

For adventitious bud formation, it is preferred that the medium contain at least one plant hormone selected from the group consisting of thidiazuron (TDZ), forchlorfenuron (CPPU), benzyladenine (BA) and naphthalene-1-acetic acid (NAA), as in the sterilizing culture and selection culture. Among all, thidiazuron is more preferable.

The concentration of the above plant hormones (total concentration) is, for example, preferably 0.1-10 mg/L, more preferably 0.5-10 mg/L, still more preferably 1-10 mg/L and especially preferably 1-6 mg/L, relative to the total medium. With respect to TDZ, the concentration is preferably 0.1-5 mg/L, more preferably 0.5-5 mg/L, still more preferably 1-5 mg/L and especially preferably 2.5-5 mg/L, relative to the total medium. With respect to CPPU, the concentration is preferably 0.1-5.0 mg/L, more preferably 1.0-5.0 mg/L and still more preferably 2.5-5 mg/L, relative to the total medium. With respect to BA, the concentration is preferably 0.1-20 mg/L, more preferably 1.0-10 mg/L and still more preferably 1.0-5 mg/L, relative to the total medium. With respect to NAA, the concentration is preferably 0.1-10 mg/L, more preferably 0.1-5 mg/L and still more preferably 0.1-1 mg/L, relative to the total medium.

By selecting the concentration of plant hormones (in particular, thidiazuron) used in redifferentiation step within the above range, the following effects can be obtained: cell division is quick; tissues with distorted morphology are suppressed to a small number; and healthy shoots with less vitrification of cells can be obtained in a large number.

Although it is a general practice that these plant hormones are not added to a medium for rooting, plant hormones may be added to the medium.

Culture for regeneration (for both adventitious bud formation and rooting) may be performed either under lighting conditions or under darkness. Culture under lighting conditions is preferable because the following effects can be obtained due to enhance of photosynthesis: formation of new tissues is promoted; and growth of healthy plant bodies is promoted. Lighting conditions at the time of culture for regeneration are not particularly limited. From the viewpoint of the above effects, the lighting conditions are preferably 50-200 µmol·m$^{-2}$·s$^{-1}$, more preferably 50-70 µmol·m$^{-2}$·s$^{-1}$.

The culture temperature for regeneration is preferably 20-33° C., more preferably 25-30° C., for example.

The period for culture for adventitious bud formation is preferably 3-8 weeks, more preferably 3-4 weeks, after two or three repetitions of subculturing to a fresh medium in every 10-14 days (i.e., after transferring to a regeneration medium), but is not particularly limited. Culture for adventitious bud formation may be terminated appropriately, for example, at a stage when formation of bladder cells as seen in the common ice plant under ordinary conditions is observed on the surface of newly developed tissues or at any stage thereafter (usually 4 to 5 weeks after the start of this culture), and transferred to a culture system for rooting.

The period for rooting is preferably 2-5 weeks, more preferably 2-3 weeks, after two or three repetitions of subculturing to a fresh medium in every 10-14 days (i.e., after transferring to a rooting medium), but is not particularly limited. Culture for rooting may be terminated appropriately, for example, at a stage when small roots (e.g. 1 cm) are formed or at any stage thereafter (usually, 2 to 3 weeks after the start of this culture).

(4) Other Steps

The production method of the present invention may comprise other steps such as described in (i) and (ii) below.

(i) Conditioning

After regeneration step, the resultant transformed common ice plant is preferably transferred to an acclimation medium and cultured there (the so-called "acclimation culture") so that the plant grows as a stable transformant.

As the acclimation medium, a known medium may be used. For example, a sterilized vermiculite or Florialite 552 (Nisshinbo) which has been impregnated with inorganic salts for MS may be used preferably.

In acclimation culture, generally, it is not necessary to positively add antibiotics or plant hormones to the medium. However, if necessary, they may be added appropriately Generally, it is preferable to perform acclimation culture under lighting conditions.

The lighting dose may be selected appropriately

The culture temperature in acclimation culture is not particularly limited. For example, it is performed preferably at preferably 20-33° C., more preferably at 20-25° C.

The period for acclimation culture is not particularly limited. For example, the period is preferably 10 days to 4 weeks, more preferably 10 days to 2 weeks.

The method of acclimation culture is not particularly limited. For example, the method described below. Briefly, adventitious buds which rooted in the regeneration step are transferred to the above-described acclimation medium. After promotion of rooting, plants with luxuriant growth of roots are transferred to, for example, a plastic box (e.g., 30 cm width×50 cm depth×15 cm height) in which vermiculite contained with sterilized water is placed. This box is covered with a plastic film or the like, and placed under the above-described lighting conditions and temperature conditions. When an appropriate period has passed from the transfer (e.g., 2 days after the transfer), holes are made in the plastic cover. When an appropriate period has passed therefrom (e.g., 4 days after the transfer), the plastic cover is removed. Subsequently (e.g., 5 days after the transfer), the plants are transferred to an artificial climate chamber adjusted to an appropriate photointensity (e.g., 350 µmol·m$^{-2}$·s$^{-1}$) and acclimatized to the intense light for a specific period (e.g., 24 hours). Then, the resultant plantlets are set in a commercial soil for plant culture (e.g., product name: Soil for Flowers and Vegetables; Kohoku Industry).

(ii) Confirmation of Gene Transfer

It is possible to examine directly whether or not a desired gene (foreign gene) has been actually transferred into the genome of the resultant transformed common ice plant. Specifically, gene transfer can be confirmed, for example, by (a) a method in which PCR is performed using appropriate primers corresponding to the nucleotide sequence of the desired gene or a part thereof, and the presence of the amplified fragment thereof is confirmed by electrophoresis or the like; or (b) a method in which a DNA fragment of the desired gene is used as a probe and hybridized to a membrane on which a chromosomal DNA isolated from the transformant and digested with an appropriate restriction enzyme has been immobilized (genomic Southern blotting). Any of the above-described confirmation methods may be performed by appropriately using means and conditions known to those skilled in the art.

4. Transformed Common Ice Plant

The transformed common ice plant of the present invention is a transformant of common ice plant in which a desired gene (foreign gene) is integrated into the genome.

As a method of producing the transformed common ice plant of the present invention, any method of obtaining a transformant of common ice plant in which a desired gene is integrated into the genome may be used, but the above-described production method of the present invention is preferably applicable. Therefore, it can be said that the transformed common ice plant of the present invention is a transformant obtainable by the above-described production method of the present invention.

The transformed common ice plant of the present invention is a transformant of common ice plant as a stable, intact plant. Therefore the plant of the present invention is extremely highly useful in function analysis of common ice plant genes, creation of improved varieties of common ice plant, and so on.

Hereinbelow, the present invention will be described with reference to the following Examples. However, the present invention is not limited to these Examples.

EXAMPLE 1

According to the procedures shown in FIG. 1 (outline), cotyledonary nodes of common ice plant were transformed with an *Agrobacterium* containing a desired gene (kanamycin resistance gene (Km$^r$: npt II)) to thereby produce a transformed common ice plant into which the above gene has been introduced. Specific methods, procedures and conditions will be described below.

(1) Obtainment of Cotyledonary Nodes

Seeds of common ice plant were sterilized with 2% hypochlorus acid for 10 minutes and seeded aseptically on 3% sucrose and 0.8% agar-added MS agar medium. Seven days after the germination, cotyledonary nodes were excised at the cotyledon leafing stage of germinated shoots. The cotyledonary node was collected from 50 plants. As the above-described "MS agar medium", the following composition was used (the same composition was also used for MS gar medium used later.)

Composition of MS Agar Medium
- Inorganic salts for MS medium (Nippon Pharmaceutical): total 4.6 g/L
  - Ammonium nitrate: 1650 mg/L
  - Potassium nitrate: 1900 mg/L
  - Calcium chloride dehydrate: 440 mg/L
  - Magnesium sulfate heptahydrate: 370 mg/L
  - Potassium dihydrogenphosphate: 170 mg/L
  - Boric acid: 6.2 mg/L
  - Manganese sulfate tetrahydrate: 22.3 mg/L
  - Zinc sulfate heptahydrate: 8.6 mg/L
  - Potassium iodide: 0.83 mg/L
  - Disodium molybdate(VI) dehydrate: 0.25 mg/L
  - Copper(II) sulfate pentahydrate: 0.025 mg/L
  - Cobalt chloride hexahydrate: 0.025 mg/L
  - Ethylenediaminetetraacetic acid disodium: 37.3 mg/L
  - Iron(II) sulfate heptahydrate: 27.8 mg/L
- Sucrose: 30 g/L
- B5 vitamins
  - Nicotinic acid: 0.01 mg/L
  - Pyridoxine hydrochloride: 0.01 mg/L
  - Thiamin hydrochloride: 0.1 mg/L
  - Myoinositol: 1 mg/L
- Agar: 8 g/L (2) Preculture of Cotyledonary Nodes The obtained cotyledonary nodes were placed on MS agar medium containing thidiazuron (TDZ: 2.5 mg/L) and cultured for 3 days.

(3) Infection in Cotyledonary Nodes with an *Agrobacterium*

(i) Preparation of an *Agrobacterium* Transformant

As an *Agrobacterium* for infecting cotyledonary nodes, EHA101 strain comprising a binary vector (pBI) which confers kanamycin resistance gene (Km$^r$), hygromycin resistance gene (Hyg$^r$) and EGFP fluorescent protein expression gene was used. Specifically, the *Agrobacterium* was transformed according to the freeze-thaw method. Briefly, 1 µg of the above-described vector (2-10 µL) was added to *Agrobacterium* competent cells in a frozen state in a 1.5 mL Eppendorf tube. This tube was capped and incubated in water bath at 37° C. for 5 minutes. Then, the tube was transferred into ice and cooled for 1 minute. One mL of YEP medium containing 50 µg/mL kanamycin was added to the tube, and the cells were cultured at 26° C. for 2 hours. Then, the cells were harvested by centrifuging (7500 rpm) at room temperature for 30 seconds. To the resultant cells, 100 µL of YEP medium containing 50 µg/mL kanamycin was added for cell lysis. The total volume of the resultant lysate was coated on YEP solid medium containing kanamycin and hygromycin both at a concentration of 50 µg/mL. The cells were spread on the surface of the medium and cultured in a dark at 26° C. for 48-72 hours until single colonies were formed.

(ii) Culture of the Transformed *Agrobacterium*

A single colony of the transformed *Agrobacterium* was inoculated into 5 mL of YEP medium and cultured overnight at 28° C. under shaking. This culture (1 mL) was mixed with sterilized, aqueous 50% glycerol solution (1 mL), and the resultant mixture was frozen at −80° C. and stored. This stock was streaked on YEP medium with a platinum loop and cultured at 25° C. under darkness for 2 days. Subsequently, colonies were suspended in 30 mL of the treated solution used in sonication, and the resultant suspension was adjusted to give a turbidity (absorbance) of 0.2 at wavelength 600 nm.

(iii) Infection in Cotyledonary Nodes

The *Agrobacterium* was suspended in a liquid medium for infection treatment containing TDZ (2.5 mg/L), acetosyringone (10 mg/L) and inorganic salts for MS medium, and the resultant suspension was adjusted to give a turbidity (absorbance) of 0.2 at wavelength 600 nm. To a 15 mL (φ 15 mm) polypropylene tube, 2.5 mL of the above suspension was added. Further, precultured cotyledonary nodes (explants) from 50 plants were added thereto. Then, the tube was dipped in a sonicator (Ultrasonic Cleaner AS-150; Iuchi Co.) for 2 seconds for sonication.

(4) Co-Culture after Infection

After sonication, the cotyledonary nodes were left in the suspension for 5 minutes. Then, excessive *Agrobacterium* suspension was removed on a sterilized filter paper. The resultant cotyledonary nodes (explants) were cultured on acetosyringone (10 mg/L)-containing agar medium (agar: 8 g/L) under lighting conditions of about 60 µmol·m$^{-2}$·s$^{-1}$ for 3 days.

(5) Sterilizing Culture

The cotyledonary nodes (explants) after co-culture were transferred to MS agar medium containing TDZ (2.5 mg/L), carbenicillin (Cb: 100 mg/L) and vancomycin (Vm: 300 mg/L) and cultured for 3 days.

(6) Selection Culture

The cotyledonary nodes (explants) after sterilizing culture were transferred to MS agar medium containing TDZ (2.5 mg/L), Cb (100 mg/L), Vm (300 mg/L) and hygromycin (Hyg: 20 mg/L) and cultured for 4 weeks in the total while subculturing once in about 2 weeks.

(7) Regeneration

The plants survived through the selection culture were placed on MS agar medium containing TDZ (2.5 mg/L). Ten to fourteen days thereafter, subculturing to a fresh medium was repeated twice or three times, and then adventitious buds were induced. Further, the resultant plants were transferred to the above-described medium without the plant hormone. Subculturing to a fresh medium was repeated twice or three times at intervals of 10-14 days to thereby induce roots.

(8) Acclimation

Rooting adventitious buds were transferred to sterilized vermiculite (or Florialite 552 from Nisshinbo impregnated with sterilized water) and gradually acclimatized to dryness and intense light.

(9) Confirmation of Transferred Gene by PCR

Figure 2:
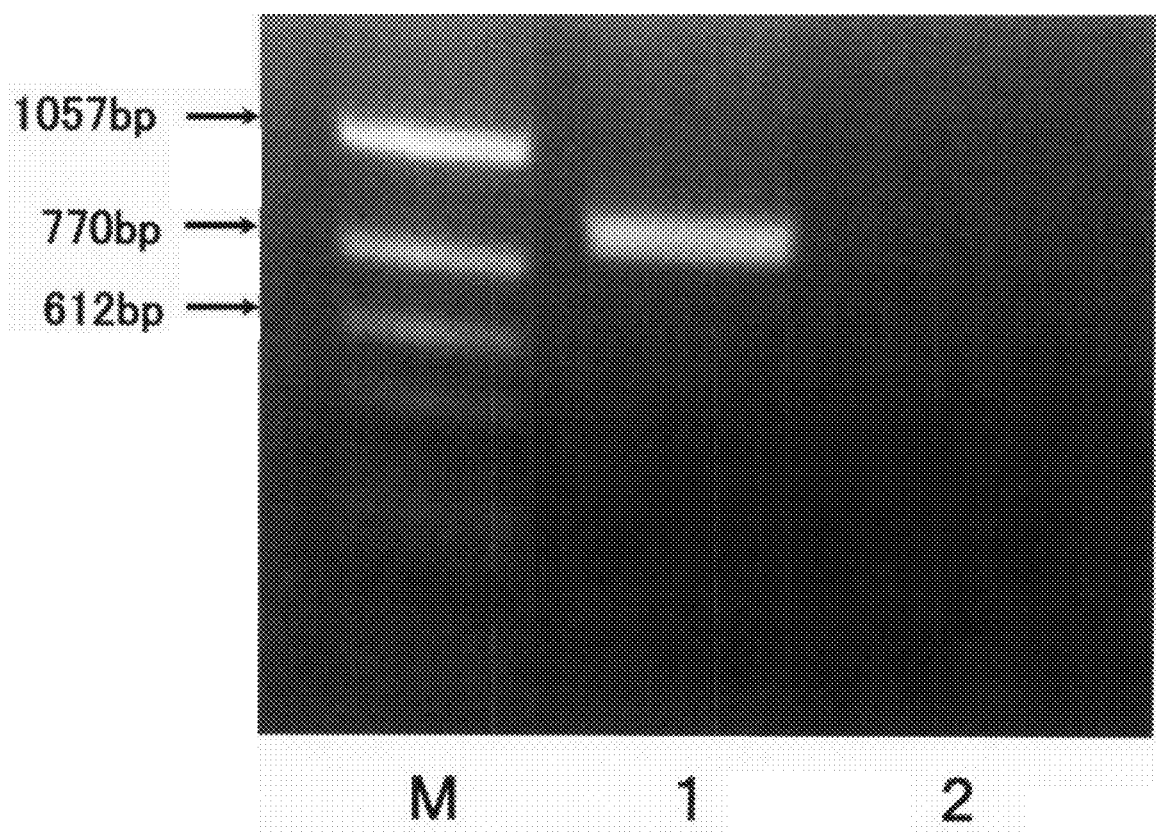
FIG. 2 is a photograph showing the results of electrophoresis of the PCR products in Example 1. In lane 1, chromosomal DNA extracted from transformants was used as a template for PCR. In lane 2, chromosomal DNA extracted from non-transformants was used as a template for PCR. Lane M shows DNA size markers.

Chromosomal DNA was extracted from the resultant transformed common ice plant by the CTAB method. Using this chromosomal DNA as a template and using the following primers based on the nucleotide sequence of Km$^r$ gene (npt II), the presence or absence of the gene (npt II) transferred by the *Agrobacterium* was examined by PCR and agarose gel electrophoresis of the PCR product. The results of this electrophoresis (photograph) are shown in FIG. 2.

```
F primer:
                                       (SEQ ID NO: 1)
GTGGAGAGGCTATTCGGCTATGACTGGGCA R primer:
                                       (SEQ ID NO: 2)
TCATAGAAGGCGGCGGTGGAATCGAAATCT
```

The PCR was performed with the following reaction solution and run for 30 cycles of thermal denaturation at 94° C. for 30 seconds, annealing at 65° C. for 60 seconds and extension at 72° C. for 60 seconds.

| Composition of PCR Reaction Solution | |
|---|---|
| Template DNA: | 1 μL |
| DNA polymerase: | 2.5 units |
| F primer: | 0.5 μL |

| Composition of PCR Reaction Solution | |
|---|---|
| R primer: | 0.5 μL |
| dNTP (2.5 mM): | 4 μL |
| 10 x Buffer: | 5 μL |
| Sterilized water: | adequate (about 38 μL) |
| Total: | 50 μL |

As shown in FIG. 2, when PCR was performed using chromosomal DNA extracted from the transformant as a template, a band of the PCR product indicating the presence of the transferred gene (npt II) was detected (lane 1); and the band was not detected in non-transformant (lane 2). Thus, it was confirmed that the desired gene was introduced into the transformant.

EXAMPLE 2

A common ice plant transformant was produced in the same manner as in Example 1 except that the medium used in preculture step for cotyledonary nodes was changed from MS agar medium containing thidiazuron (TDZ: 2.5 mg/L) to MS agar medium containing two plant hormones of thidiazuron (TDZ: 5 mg/L) and naphthalene-1-acetic acid (NAA: 0.1 mg/L).

The survival ratio after transformation (%) and shoot regeneration ratio (%) relative to the number of cotyledonary nodes used for transformation (from 50 plants) were compared between Example 1 (2.5 mg/L TDZ) and Example 2 (5 mg/L TDZ and 0.1 mg/L NAA). The results are shown in FIG. 3 (graph).

Figure 3:
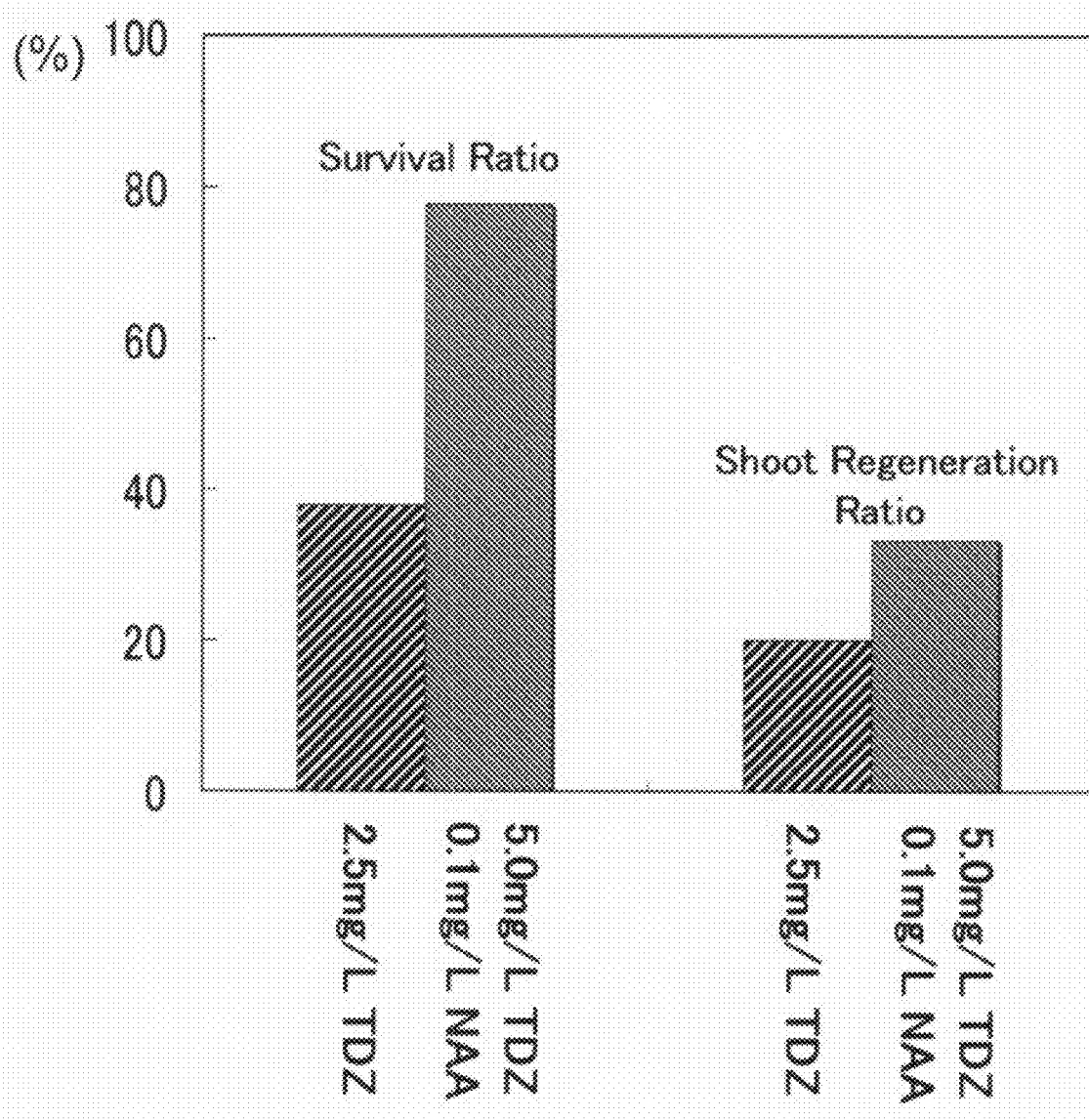
FIG. 3 is a graph showing the effects of plant hormone compositions in the pre-culture medium on transformation efficiency of common ice plant (survival ratio and shoot differentiation ratio).

From FIG. 3, it was confirmed that both survival ratio and shoot differentiation ratio are improved by selecting a specific combination of plant hormones and specific concentrations as selected in Example 2.

INDUSTRIAL APPLICABILITY

According to the present invention, it is possible to provide a method of transforming common ice plant by gene transfer using a microorganism belonging to the genus *Agrobacterium* which has been impossible to date; a method of producing a transformed common ice plant; and a transformed common ice plant as a stable, intact plant. Therefore, the present invention can be said extremely useful, for example, in functional analysis of common ice plant genes and creation of improved varieties of the common ice plant.

SEQUENCE LISTING FREE TEXT

SEQ ID NO: 1: primer
SEQ ID NO: 2: primer

The invention claimed is:

1. A method of transforming a common ice plant, which method comprises:
   pre-culturing a cotyledonary node in a medium comprising at least thidiazuron;
   co-culturing the cotyledonary node with a microorganism belong to the genus *Agrobacterium* containing a desired gene in a medium comprising acetosyringone; and
   culturing a transformed cotyledonary node in a regeneration medium comprising at least thidiazuron, thereby generating adventitious buds.

2. The method according to claim 1, wherein said cotyledonary node is a cotyledonary node of a plantlet.

3. The method according to claim 2, wherein said plantlet is a plantlet 4 to 10 days after seeding.

4. The method according to claim 1, wherein the pre-culture medium further comprises at least one plant hormone selected from the group consisting of forchlorfenuron, benzyladenine and naphthalene-1-acetic acid.

5. The method according to claim 4, wherein the total concentration of the plant hormone is 0.1-10 mg/L.

6. The method according to claim 1, wherein the concentration of thidiazuron is 0.1-5 mg/L.

7. A transformed common ice plant obtained by the method according to claim 1.

8. The transformed common ice plant according to claim 7, wherein a desired foreign gene is integrated into its genome.

* * * * *